United States Patent [19]

Traina

[11] Patent Number: 4,630,482
[45] Date of Patent: Dec. 23, 1986

[54] METHOD AND APPARATUS FOR ULTRASONIC MEASUREMENTS OF A MEDIUM

[76] Inventor: John Traina, 303 N. Rose Dr., Glenshaw, Pa. 15116

[21] Appl. No.: 745,725

[22] Filed: Jun. 17, 1985

[51] Int. Cl.$^4$ ............................................ G01N 29/00
[52] U.S. Cl. .................. 73/597; 73/861.28; 73/24
[58] Field of Search .............. 73/597, 861.28, 24; 367/126, 127

[56] References Cited

U.S. PATENT DOCUMENTS

| | | | |
|---|---|---|---|
| 2,923,155 | 2/1960 | Welkowitz | 73/861.26 |
| 2,959,054 | 11/1960 | Welkowitz | 73/861.02 |
| 3,020,759 | 2/1962 | Welkowitz | 73/861.26 |
| 3,178,940 | 4/1965 | Dahlke et al. | 73/861.26 |
| 3,188,862 | 6/1965 | Roth | 73/861.02 |
| 3,858,446 | 1/1975 | Flemons | 73/861.06 |
| 4,114,439 | 9/1978 | Fick | 73/597 |
| 4,119,950 | 10/1978 | Redding | 340/524 |
| 4,183,244 | 1/1980 | Kohno et al. | 73/861.26 |
| 4,202,210 | 5/1980 | Multon et al. | 73/861.26 |
| 4,312,239 | 1/1982 | Zalessky et al. | 73/861.29 |
| 4,334,434 | 6/1982 | Appel et al. | 73/861.29 |
| 4,389,899 | 6/1983 | Krause | 73/861.28 |
| 4,442,719 | 4/1984 | Allen | 73/861.29 |
| 4,475,406 | 10/1984 | Ansaldi et al. | 73/861.29 |
| 4,490,831 | 12/1984 | Poston et al. | 375/94 |
| 4,542,656 | 9/1985 | Johnson | 73/861.28 |

Primary Examiner—Anthony V. Ciarlante
Attorney, Agent, or Firm—Buell, Ziesenheim, Beck & Alstadt

[57] ABSTRACT

A method and apparatus for measurement of time required for an ultrasonic tone burst to traverse a medium from a transmitter to a receiver is disclosed. Two transducers separated by a distance through which a medium flows alternatively act as a transmitter and then a receiver of ultrasonic signals. After a signal has been emitted from the first ultrasonic transducer, the second transducer is electronically checked for receipt of the ultrasonic signal. That checking is done at certain time intervals, preferably 4 microseconds, over a selected period of time. Samples are taken over each time interval. For each sample time slot the presence and strength of an output signal is measured. An address in a memory is selected which corresponds to each sampling time slot. Each input sample is stored in memory at an address which corresponds to the time slot at which the input sample was taken. This procedure is repeated for several time intervals of the same length using subsequent ultrasonic signals from the transducer. On each subsequent transmission the input samples are combined to the input samples stored in the memory thereby producing a corresponding new process sample at each address. The process samples are periodically examined and preferably compared to a threshold level. Whenever one process sample reaches this threshold level, the time which corresponds to the time slot containing that new process sample is identified. The identified time is then taken as the time required for the signal to transverse the medium. This time can then be used to calculate various properties of the material which was traversed including the speed of sound and true gaseous flow independent of temperature, turbulance and density of the medium, distance, specific heat ratio of the medium being transversed, carbon dioxide concentration in the medium and temperature over a line path.

22 Claims, 5 Drawing Figures

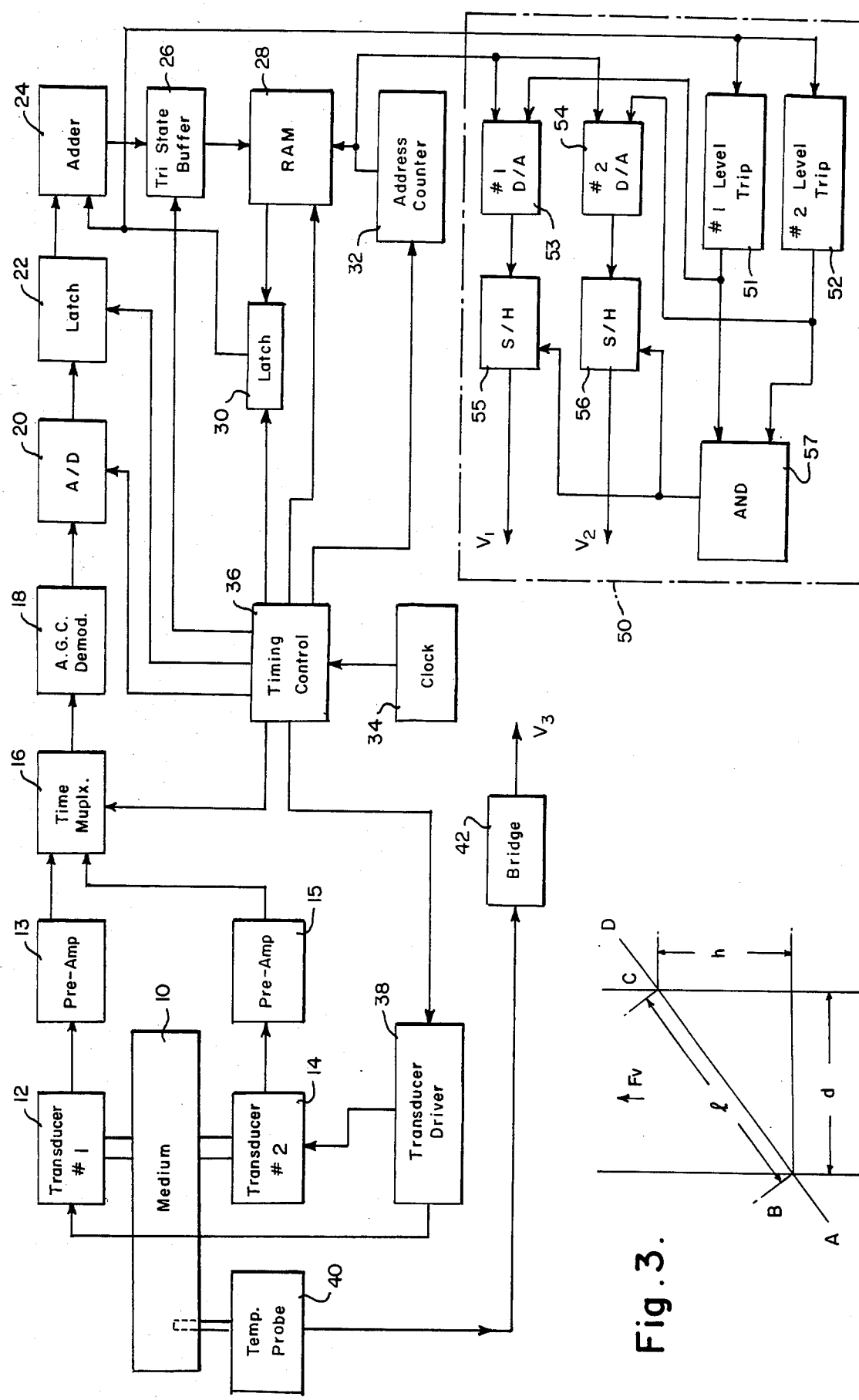

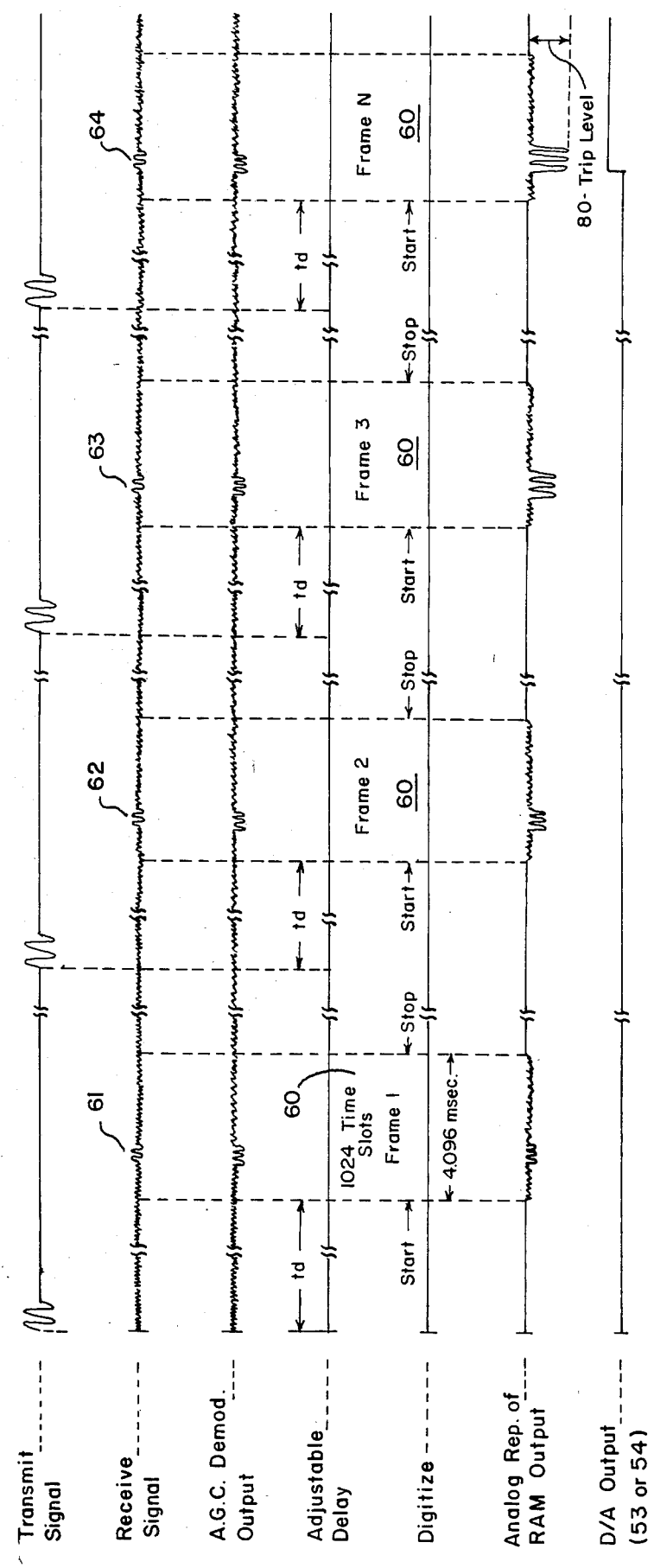

METHOD AND APPARATUS FOR ULTRASONIC MEASUREMENTS OF A MEDIUM

NATURE OF THE INVENTION

The invention relates to the field of ultrasonic measurements and more particularly to method and apparatus for the measurement of the time required for an ultrasonic tone burst to traverse a medium from a transmitter to a receiver. The device can perform well with mediums that are at high temperature and have high attenuation as well as high turbulence.

After the time has been measured that information can be used in at least six ways. First, I can measure true gaseous flow even at elevated temperatures with turbulent mediums. Second, I can measure the speed of sound independent of temperature, turbulence, and the density of the medium. Third, I can use this informtion for measuring distance. Fourth, I can determine the specific heat ratio of the medium being transversed. Fifth, as a fairly specific application of measuring the change in the specific heat ratio, I can measure the carbon dioxide concentration. With the sixth application, I can accurately measure the temperature over a line path.

DESCRIPTION OF THE PRIOR ART

Prior art devices have used ultrasonics in the measurement of flow in tubes or conduits. In general, these prior art devices are used for true liquid flow and not in true gases. Many of them are inserted into the path of the liquid or gas. But, to avoid error, it is desirable that the fluid's movement not be disturbed during measurement by the insertion of a measuring device into the stream. My method and apparatus do not impede fluid flow. Many fluids such as stack gases contain highly abrasive and corrosive materials at elevated temperatures. Consequently, it is important that any apparatus used to measure the flow of such material be able to withstand the adverse atmosphere within the pipe. Many prior art devices cannot be used for gases which are high temperatures and those which may contain abrasive or corrosive materials. Other methods and devices can only withstand short exposures to high temperatures, abrasives or corrosive materials.

It is well known that the transmission of ultrasonic signals through a medium depends not only on the flow rate of the medium but also upon its density, temperature, and whether or not it is a homogeneous material. Consequently, the flow meters of the prior art must be calibrated each time they are used to account for these differences among fluids. Any change in fluid temperature after calibration could cause the ultrasonic flow meter of the prior art to provide an erroneous reading. Additionally, any change in the makeup of the medium could also create erroneous readings. There is a need for a flow meter which is not dependent upon temperature and density changes and which can be used without recalibration whenever the fluid being measured changes.

Because the art recognizes that typical flow rate measurements are temperature and density dependent, many techniques require a temperature reading of the fluid immediately before or during the use of the flow meter. This practice has at least three problems. First, insertion of a temperature probe into the stream may affect the fluid flow. Second, it is frequently difficult to put a temperature sensor in the conduit at the location where the flow is being measured. Further, any measurements of temperature taken at a point remote from the position of the ultrasonic flow meter or at a different point in time may differ from the actual temperature at the time and place of the flow meter reading. There is a need for a flow meter which avoids these problems.

In recent years much concern has developed over the emission of pollutants into our atmosphere. The Environmental Protection Agency and other government regulatory agencies have established certain pollution emission standards. Typically, these standards define the parts of pollutant per volume of gas which can be emitted per unit of heat contained in the fuel that produced the gas. It is well known that the volume of gas emitted can be calculated by multiplying the cross-sectional area of the conduit times the flow rate of the fluid. Knowing the volume of gas that is emitted, one can measure a pollutant and calculate the actual amount of pollutant being emitted from the conduit. Many sources need to know the actual pollutant emissions either for regulator or operational reasons. Present art devices that measure pollutants cannot give the actual emissions by any direct means.

The principal source of air pollution are the coal fire electric utility plants. Efforts have been made to constantly monitor the flow of stack gases in these plants. Because of the high temperatures, abrasive content and corrosive materials contained in stack gases, no prior art flow meter has been capable of constantly and accurately monitoring stack gas flow over an extended period without repeated calibration. Consequently, utilities must rely on sampling techniques to determine the amount of pollutants escaping from their plants. With this technique it is impossible to accurately determine emissions because flow rates change over time. Yet, prior to my invention no more accurate methods of measurement have been available. There is a need for a flow meter which will be suitable to constantly monitor stack gases over an extended period of time.

SUMMARY OF THE INVENTION

An object of the invention is to provide a method of measuring the time required for an ultrasonic tone burst to traverse a medium. Then I use that measurement to calculate a variety of properties of the medium. My method is simple to carry out and ensures greater accuracy. One object of the invention is to provide an apparatus to carry out the method of ultrasonic measurement which apparatus can be used to measure stack gas flow rates and other fluids which contain abrasive or corrosive materials and are at elevated temperatures.

The method of ultrasonic measurement of the present invention utilizes two transducers separated by a distance. Each transducer alternately acts as a transmitter and then a receiver of ultrasonic signals. One transmitter will emit a tone burst, it will traverse the medium to be received by the other transducer where in turn that transducer will transmit a tone burst and it will be received by the original transducer. In this manner the medium is traversed in both directions.

After a signal has been emitted from the first ultrasonic transducer, I electronically check the second transducer for receipt of the ultrasonic signal. That checking is done at certain time intervals, preferably 4 microseconds, over a selected period of time. I prefer to sample 1,024 times over a period of 4.096 milliseconds. A sequence of input samples is produced, one for each sample time slot, according to the presence and strength of the output signal at each time slot. An address in a memory is selected which corresponds to each time slot and the input sample is stored in memory at the address which corresponds to the time slot at which the input sample is taken. This procedure is repeated for several time intervals using subsequent ultrasonic signals from the transducer. On each subsequent transmission the input samples are combined, preferably added, to the input samples stored in memory thereby producing a corresponding new process sample at each address. The process samples are examined, preferably compared, to a threshold value. Whenever one process sample reaches the threshold value the time corresponding to the time slot containing that new process sample is identified. As will be seen, this time can then be used to calculate the various properties of the material which was traversed.

Other objects and advantages of the present invention will become obvious from a description of the present preferred embodiments of my apparatus and present preferred methods of measuring material flow.

BRIEF DESCRIPTION OF THE DRAWINGS

FIG. 1 is a block diagram of an embodiment of the apparatus.

FIG. 2 is a diagram showing how the input samples are maintained at an address and added together until they reach a threshold value.

FIG. 3 is a diagram showing relevant distances on a conduit in which the medium is present.

DESCRIPTION OF PRESENT PREFERRED EMBODIMENTS

Figure 4:
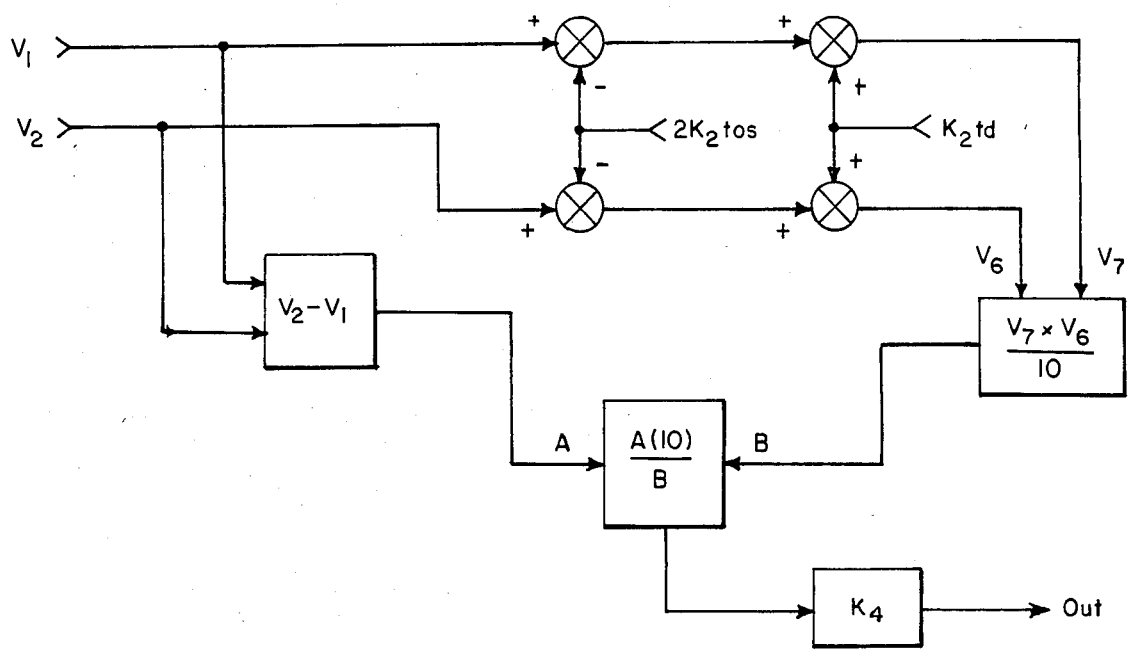
FIG. 4 is a present preferred analog circuit for calculating flow rate.

In FIG. 1, I have illustrated a medium 10 to be measured 10, having transducers 12 and 14 mounted on the sides of the medium substantially opposite one another. The transducers are connected to respective preamplifiers 13 and 15. The preamplifier output is sent to a time multiplexer 16 which sends alternately preamplifier 13's output and preamplifier 15's output to the Automatic Gain Control (AGC) demodulator 18.

The AGC demodulator 18 is a device which performs two functions, automatic gain control and demodulating. For high turbulence environments, it is imperative that an automatic gain control is used to accommodate the high amplitude dynamic range of such signals. The demodulator converts the tone burst into a unidirectional going signal. Both full-wave and half-wave demodulators have been used. The full-wave demodulator will give lower granularity to the output, whereas the half-wave will give a smoother output. The analog to digital (A/D) convertor 20 receives the signal from the AGC demodulator circuit and digitizes a portion of the received wave form. This digitized output, which in my present, preferred design consists of over a thousand words per received signal, ultimately arrives and is stored in the RAM 28. The loop consisting of the adder 24 the tristate buffer 26 the RAM 28 and its latch 30 improves the signal-to-noise ratio of the received signal considerably as follows: when the number one transducer 12 transmits a tone burst, it ultimately is received by the number two transducer 14. At a given time after the transmit, but prior to the arrival of that burst signal, the A/D convertor 20 starts converting the signal from the number two preamplifier into digital words. Each word is a small given time increment from the previous one. Each word is latched by latch 22 and presented to the adder. The first time through the RAM 28 will be zero, and therefore, the adder output will not be any different than the A/D latch output. The RAM 28 in the present preferred design, uses 1,024 words to represent the preamplifier 15 output over a given time period. When transducer 14 transmits, transducer 12 will ultimately receive the signal. The A/D convertor 20 again starts to convert the analog voltage into digital words beginning sometime before the arrival of the burst signal at transmitter 12. These words are sent around the loop in the same way as the signal received by transducer 14. The RAM 20 stores the signal received from transducer 12 as 1,024 words in different locations than the signal received words from transducer 14. The next time that transducer 12 transmits, transducer 14 and preamplifier 15 will give a received signal and the A/D convertor 20 will create another set of digital words. Each of these words will be presented to the adder 24 along with the word that the RAM stored for that same given time the last time transducer 12 transmitted. The adder 20 will now put that sum into the tristate buffer 26 and the location in the RAM 20 will now be updated to the sum. This will be done for every word of the 1,024 words generated for that received signal. This process will be repeated when the transducer 14 transmits and is received by the transducer 12. The timing of signal transmissions by transducers 12 and 14 is controlled by clock 34 timing control 36 and transducer driver 38. Each subsequent received signal will be added again to the sum of the ones that came before it. The result is that non-random signals will be enhanced to a far greater degree than random ones. If one were to look at an analog equivalent of the RAM output between the latch 30 and the adder 24 with the system in operation, the received signals could be seen growing in amplitude in respect to the noise (See FIG. 2). A level detection circuit 50 looks at the amplitude of this added digital signal. When a word is sufficiently large, it will trip the appropriate #1 or #2 latch 51 or 52. Latches 51 and 52 are looking at the address counter for the RAM. The result is that the latches 51 and 52 store the address of the first word in each group of 1,024 that reaches the level detector's trip point. Since the address counter 32 moves from one word to the other at a very specific rate and is correlated to the A/D convertor's rate, the address of the word represents the time from the beginning of the A/D conversions that the received tone burst arrived. This address is latched into the appropriate latch 51 or 52 and in the present preferred design is converted to an analog voltage by the digital-to-analog convertors 53 and 54.

There is a sample and hold 55 and 56 used on each of these analog voltages so that V1 and V2 are updated as commanded by AND Function 57 simultaneously as opposed to when latch 51 or 52 is tripped. The latch 51 and latch 52 cannot trip at the same time, nor will they trip close enough to the same time to be considered the same in turbulent environments. After 55 and 56 have been updated, all RAM locations are initialized to zero and the processing repeated. In addition to the transducer processing system, a temperature probe 40 with a precision Wheatstone bridge 42 is shown to be developing a voltage V3. In certain applications of the invention, this voltage is used.

There are many readily available components which can be used for the circuit of FIG. 1. Each of the major components is made by several manufacturers. Thus, those skilled in the art are free to select such items from among several sources. I have found the following products to work well in my circuit.

| Name | Drawing Reference Number | Major Component | Source |
|---|---|---|---|
| Time Multiplexer | 16 | FET Switch IT401 | Intersil |
| AGC Demodulator | 18 | AD534 | Burr-Brown |
| A/D Converter | 20 | HSADC82 | Hybrid Systems |
| Latch | 22,30 | 74273 | Texas Instr. |
| Adder | 24 | 74283 | Texas Instr. |
| Tri-state Buffer | 26 | 74244 | Texas Instr. |
| RAM | 28 | TC5516 | Toshiba |
| Address Counter | 32 | CD4040 | RCA |
| D/A Converter | 53,54 | HSDAC80-CBI-V | Hybrid Systems |
| Level Trip | 51,52 | 7411 | Texas Instr. |
| Sample and Hold | 55,56 | LH0042 | Nat. Semicon. |
| Clock | 34 | MC741A1-071 | McCoy |
| Timing Control | 36 | 74164 | Texas Instr. |
| Transducer Driver | 38 | MTP25NO5 | Motorola |
| Temperature Probe | 40 | PR-11-2-200-1/4-72 | Omega |

FIG. 2 shows a diagram of a few time frames 60 used in my present preferred embodiment. The sections 61 through 64 indicate the receipt of signals during various time frames. The top line labeled "Transmit Signal" shows the signal transmitted by transducer 12 or 14 in various time frames. That signal is received at some later time as indicated by the second line labeled "Received Signal". The received signal is processed by the AGC Demodulator which generates an output shown in the third line. The Adjustable Delay line illustrates that sampling at selected intervals is done through the time frame whose duration is adjustable. The sampled signal is digitized as indicated by the fifth line. The sixth line shows an analog representation of the RAM output. It can be seen that summation of signals occurs until the threshold or trip level 80 is reached. At that point the address is latched in a D/A convertor 53 or 54 which generates an output shown in the bottom line of FIG. 2. That output identifies the average time which the ultrasonic signal from the transducers has taken to traverse the medium. It should be apparent from FIG. 2 that the signals will vary in intensity at each time slot. This variation in intensity may be caused by not only the presence or absence of a signal but temperature fluctuation, impurities or even a change in composition of the fluid. Since my processor is programmed to take an average of the times at which a threshold value is reached, it is less sensitive to such fluctuations and more likely to identify the correct time at which the signal arrives. Having described my method and apparatus for measuring the time during which an ultrasonic signal traverses a medium, I now turn to the use of this time to determine characteristics of the medium. This determination is made by further processing voltages $V_1$ and $V_2$ In some applications $V_3$ will be used as a temperature indication and in some applications it will not.

Flow Rate

Flow rate can be calculated mathematically from either voltages $V_1$ and $V_2$ or from the digital equivalent in the D/A latches using a variety of electronic calculating techniques known to the art. Accordingly, it is only necessary to explain the calculation here. We begin by referring to FIG. 3, which is a diagram of a medium 10 shown transducers 12 and 14 at points A and D. The conduit's diameter is shown as d, the path of the tone through the conduit is L, and h is the height of a right triangle including d and L. B and C are points on the side of the conduit through which the tone passes. Thus L equals the distance from B to C. Distances from A to B and from C to D are the space between the transducers 12 and 14 and the side of conduit 10.

If a tone burst leaves A toward D, the time to traverse the distance may be expressed:

$$t_{AD} = t_{AB} + t_{BC} + t_{CD} \qquad (1)$$

since the whole equals the sum of the parts. Given that rate multiplied by time equals distance:

$$R\,T = D \qquad (2)$$

and the distance from B to C equals $$L = D_{BC} = \sqrt{d^2 + h^2}$$

the time required for the tone burst to travel from B to C may be expressed:

$$T = \frac{D}{R} = \boxed{t_{BC} = \frac{L}{R}} \qquad (3)$$

Where R is the vector sum of the velocity of sound and the flow velocity.

$$\vec{R} + \vec{C_s} + \vec{F_v} \qquad (4)$$

Where: $\vec{C_s}$ is Velocity of Sound
The magnitude of R is:

$$|\vec{R}| = |\vec{C_s}| + |\vec{F_v}| \left( \sin\left( \arctan \frac{h}{d} \right) \right)$$

$$R = C_s + F_v \left( \sin\left( \arctan \frac{h}{d} \right) \right) \qquad (5)$$

letting:

$$K_1 = \sin\left( \arctan \frac{h}{d} \right)$$

R becomes:

$$R = C_s + F_v(K_1) \qquad (6)$$

Equation #3 l now becomes:

$$t_{BC} = \frac{l}{C_s + F_v(K_1)} \qquad (7)$$

Similar to equation #1, the time required to traverse the distance from D to A is:

$$t_{DA} = t_{DC} + t_{CB} + t_{BA}$$

Using a similar development to that used for equations #2 through #7 for the time required to traverse from C to B yields:

$$t_{CB} = \frac{l}{C_s - F_v(K_1)} \tag{9}$$

Rearranging and subtracting equation #9 from #7;

$$C_s + F_v(K_1) = \frac{l}{t_{BC}} \tag{10}$$

$$\underline{C_s - F_v(K_1) = \frac{l}{t_{CB}}}$$

$$2F_v(K_1) = \frac{l}{t_{BC}} - \frac{l}{t_{CB}}$$

Rearranging equation #10:

$$F_v = \frac{l}{2K_1}\left(\frac{1}{t_{BC}} - \frac{1}{t_{CB}}\right) \tag{11}$$

Changing the form:

$$F_v = \frac{l}{2K_1}\left(\frac{t_{CB} - t_{BC}}{(t_{CB})(t_{BC})}\right) \tag{12}$$

Note that equation #12 is independent of Cs, which means that those variables which affect Cs, temperature, density, etc., do not affect the measurement of the flow velocity, Fv. Therefore, the flow is measured to an accuracy limit essentially by the accuracy of the traverse time measurement.

To convert Fv to Flow, multiply by A where A is the effective cross sectional area of the stack, duct, pipe, or conduit. The equation for Flow is:

$$F = \frac{Al}{K_1}\left(\frac{t_{CB} - t_{BC}}{(t_{CB})(t_{BC})}\right) \tag{13}$$

In the preferred embodiment, V1 and V2 are capable of each being 0 to +10 V depending on the address of the word that trips the latch. The two voltages are proportional to the number out of the address counter at the time of the trip. In the present design, the receiver signal is digitized every four microseconds. Therefore, each count of the address counter represents a four microsecond increment of time. Noting that the digitizing does not start for a time (td) after the transmit and that there are 1,024 address locations, the following relations may be written:

$$V_1 = K_2(t_{AD} - t_d) \tag{14}$$

$$V_2 = K_2(t_{DA} - t_d) \tag{15}$$

Where $K_2 = \frac{10 \text{ volts/sec}}{(1024)(4 \times 10^{-6})}$

For applications where the medium is destructive to the transducers, a purge system is used to prevent the medium from passing from B to A or from C to D. For most applications, the time for the sound to travel these typically short distances can be considered to be the same. (A better approximation: $t_{AB} = t_{DC}$ and $t_{BA} = t_{CB}$). Therefore:

$$t_{AB} = t_{CD} = t_{BA} = t_{CD} = t_{OS} \tag{16}$$

Substituting Equations #16 into #1 and #8, Equations #1 and #8 become:

$$t_{AD} = t_{BC} + 2t_{OS} \tag{17}$$

$$t_{DA} = t_{CB} + 2t_{OS} \tag{18}$$

Substituting Equations #17 and #18 into #14 and #15 yields:

$$V_1 = K_2(t_{BC} + 2t_{OS} - t_d) \tag{19}$$

$$V_2 = K_2(t_{CB} + 2t_{OS} = t_d) \tag{20}$$

Rearranging Equation #19 and #20:

$$t_{BC} = \frac{V_1}{K_2} - 2t_{OS} + t_d \tag{21}$$

$$t_{CB} = \frac{V_2}{K_2} - 2t_{OS} + t_d \tag{22}$$

Equations #21 and #22 substituted into #13 gives:

$$F = \frac{AlK_2}{K_1}\left[\frac{V_2 - V_1}{(V_2 - 2K_2t_{OS} + K_2t_d)(V_1 - 2K_2t_{OS} + K_2t_d)}\right] \tag{23}$$

This equation may be implemented in several ways. I prefer to use the analog circuit shown in FIG. 4. That circuit is fairly simple and can be readily understood by referring to Equation 23. Values shown in FIG. 4 are derived from the equations discussed above. $K_4$ is chosen so that FS=10 volts.

For some applications a problem will arise if K2 is large because (K2)(td) can exceed maximum voltage available. Dealing with the problem K2td will be attenuated by K3, Equation #23 then becomes:

$$F = \frac{Al_{BC}K_2}{K_1K_3}\left[\frac{V_2 - V_1}{\left(\frac{V_2}{K_3} - 2\frac{K_2}{K_3}t_{OS} + \frac{K_2}{K_3}t_d\right)\left(\frac{V_1}{K_3} - 2\frac{K_2}{K_3}t_{OS} + \frac{K_2}{K_3}t_d\right)}\right] \tag{24}$$

Figure 5:
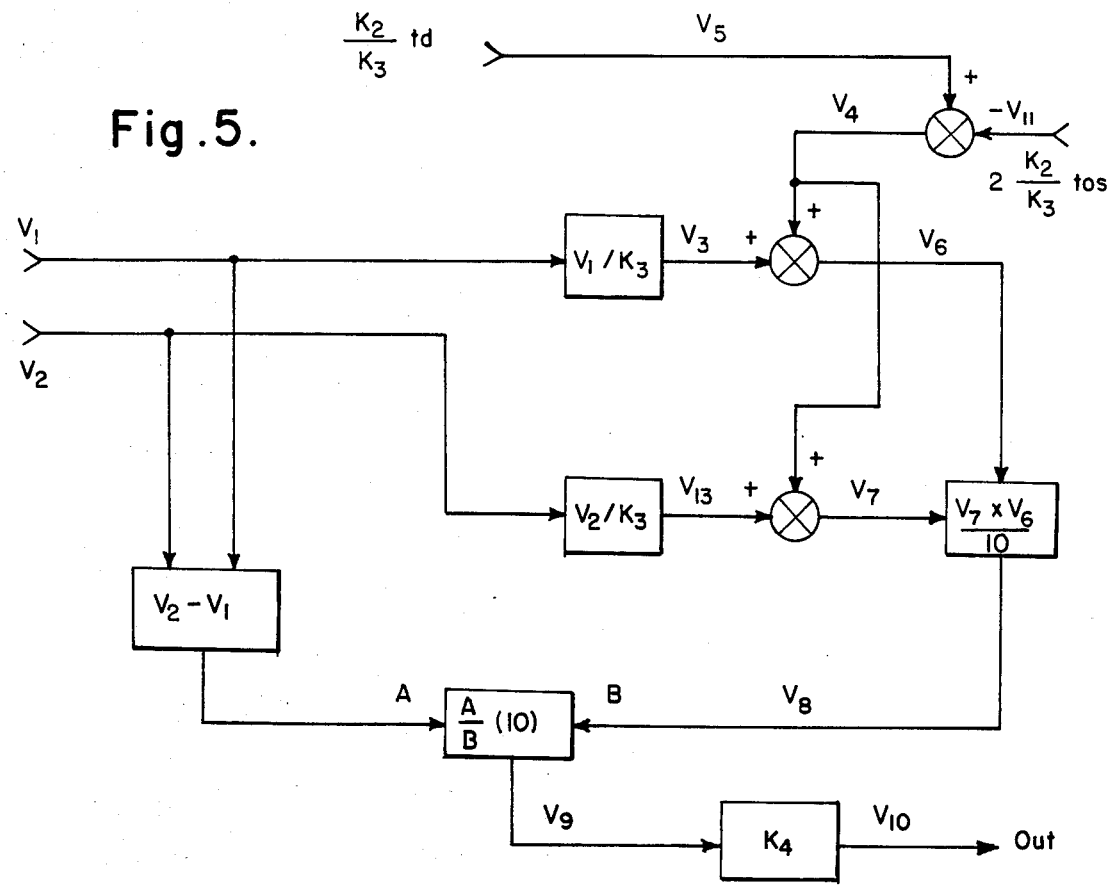
FIG. 5 is a second present preferred analog circuit for calculating flow rate.

This equation can be solved by the analog circuit of FIG. 5. Again $K_4$ is chosen so that FS=10 volts. The output voltage of this circuit is $V_{10}$. That voltage may be expressed as:

$$V_{10} = 100 K_4\left[\frac{V_2 - V_1}{(V_2 + [V_5 - V_{11}])(V_3 + [V_5 - V_{11}])}\right] \tag{25}$$

$$V_{10} = 100 K_4 \left[ \frac{V_2 - V_1}{\left(\frac{V_2}{K_3} + V_4\right)\left(\frac{V_1}{K_3} + V_4\right)} \right] \quad (26)$$

I prefer to use Equation #26. I have found this method to have worked successfully in a stack 16.5 feet in diameter, 280 degrees Farenheit and 500 KCFM.

Referring to the block diagram of FIG. 1, an alternate procedure would be to send the latched digital address words directly to a digital processor. Whether digital or analog processing is used, the speed of sound does change with temperature and other variables. The delay time (td) will need to be altered if the speed of sound changes such that the received tone burst does not fall in the digitized portion. In the analog version this is done by changing td if either V1 or V2 gets too close to zero or ten volts. In a digital version, if the address that is latched is too near zero or 1,024, then td must be changed. The present embodiment allows for the digital control of this delay. When td was altered, the appropriate scaling is automatically done to V5 in FIG. 4 or FIG. 5.

An excellent feature of the invention is the fact that the system calibration may be checked using the actual transducers through the medium. This is accomplished by letting the digital signal enhancement circuit process receiver signals from only one transducer as if they came from two in an alternate manner. The result is an indication of zero flow since the time to traverse is equal (refer to Equation #13). The zero occurs regardless of which transducer is used. A repeatable up scale calibration check is performed by the same technique as the "zero" except that every other receiver tone burst is delayed by a known amount with the denominator of Equation #26 set to a fixed value.

Speed of Sound Measurement

The invention measures the speed of sound in applications where other methods will not work. Under the same type of adverse conditions as the flow monitor (high attenuations, high temperatures, high turbulence destructive medium) the speed of sound is measured.

In addition, the speed of sound may be measured even where the medium has flow. Rearranging and now adding Equation #7 and Equation #9:

$$C_s + F_v(K_1) = \frac{l}{t_{BC}}$$

$$C_s - F_v(K_1) = \frac{l}{t_{CB}}$$

$$2C_s = l\left(\frac{1}{t_{BC}} + \frac{1}{t_{CB}}\right)$$

$$C_s = \frac{l}{2}\left(\frac{t_{BC} + t_{CB}}{(t_{BC})(t_{CB})}\right) \quad (27)$$

Note that Equation #27 is independent (Fv). This means that the speed of sound is determined accurately even where there is flow. Equation #27 is very similar to Equation #12 and may be implemented similarly in either an analog or digital manner.

The applications where both the flow and the speed of sound are required to be measured can be accomplished with very little additional hardware over that required for either.

Referring to FIG. 4, only the block that subtracts V2 from V1 need be alerted to yield a voltage proportional to the speed of sound at $V_{10}$.

Distance Measurement

To use the invention to measure distance, the temperature input is needed. The invention works on the fact that in many media the speed of sound is well known as a function of temperature. For example, a reasonably good equation for the speed of sound in dry air is:

$$C_{DA} = 331.3 \sqrt{1 - \frac{T}{273}} \quad (28)$$

T is in degrees C $C_{DA}$ is the speed of sound from D to A (or A to D) in Meters/sec Rearranging Equation #27:

$$l = 2C_s\left(\frac{t_{BC} t_{CB}}{t_{BC} + t_{CB}}\right)$$

To use the invention to measure hte distance (l) in dry air, $CS=C_{DA}$ giving the equation:

$$l = 2(331.3)\sqrt{1 - \frac{T}{273}}\left(\frac{t_{BC} t_{CB}}{t_{BC} + t_{CB}}\right)$$

Referring to FIG. 1, V3 serves as the T input in the computing algorithm. Equation #30 may then be implemented in either a digital or analog manner.

Determining The Ratio of the Specific Heats of the Media

The speed of sound for a gas may be expressed:

$$C = \sqrt{\gamma RT}$$

Where R is gas content and where $$\gamma = \frac{C_p}{C_v} \quad (32)$$

Cp and Cv are the specific heats of the gas at constant pressure and constant volume respectively. By knowing the speed of sound and the temperature, the ratio of the specific heats is determined.

Substitute Equation #31 into Equation #27:

$$\sqrt{\gamma RT} = \frac{l}{2}\left(\frac{t_{BC} + t_{CB}}{t_{BC} t_{CB}}\right) \quad (33)$$

Solving for $\gamma$:

$$\gamma = \left[\frac{l}{2R^{\frac{1}{2}}T^{\frac{1}{2}}}\left(\frac{t_{BC} + t_{CB}}{t_{BC} t_{CB}}\right)\right]^2 \quad (34)$$

Equation #34 is more easily implemented as $$\gamma = \frac{l^2}{4RT}\left(\frac{t_{BC} + t_{CB}}{t_{BC}t_{CB}}\right) \quad (35)$$

While using the speed of sound for determining the ratio of the specific heats has been done by prior art devices, this invention allows the measurement to be performed under the adverse conditions already described.

Measuring Carbon Dioxide Concentration

As Equation #35 shows, the ratio of the specific heats is readily found using this invention. The fact that the invention performs the measurement where the medium is corrosive, moving, and at high turbulence and temperature allows the carbon dioxide concentration to be measured in a discharge stack, duct pipe, or conduit of fossil fuel fire apparatus. This is done by empirically determining the ratio of the specific heats as a function of carbon dioxide. Data is established in the laboratory for the specific medium (discharge from coal, oil, gas, or other combustion) at or near the temperature at which it will be measured.

The invention is installed and the ratio is corrected to carbon dioxide concentration based on the data.

Temperature Measurement

Looking at Equation #27:

$$C_s = \frac{l}{2}\left(\frac{t_{BC} + t_{CB}}{t_{BC}t_{CB}}\right) \quad (36)$$

Where the distance (l) is known, Cs is accurately measured as described in the speed of sound measurement. The temperature can be measured in a medium where there is or can be created an algorithm that states the speed of sound as a function of temperature. For dry air, the speed of sound is:

$$C_{DA} = 331.3\sqrt{1 - \frac{T}{273}} \quad (37)$$

Substitute Equation #37 in $$T = \left[1 - \left(\frac{l}{(2)(331.3)}\left(\frac{t_{BC} + t_{CB}}{(t_{BC})(t_{CB})}\right)\right)^2\right]273 \quad (38)$$

My apparatus and method allows the user to measure temperature along a designated line. This is opposed to the point measurement done by most other devices. The fact that the line can be through the type of adverse medium already mentioned greatly enhances the number of applications not served by other devices.

EXAMPLE

I have tested the device in a smoke stack to measure gas flow. The stack was a cylinder with a diameter of 16.5 ft. Referring to FIG. #3, the following values described the test configuration:
 h=10.0 ft
 d=16.5 ft
 A=214 ft²
 L=19.3 ft
 $K_1$=0.5183 ($K_1$=sin (arc tan h/d ))
 $K_2$=10 V/4.096 msec
 td=12 msec
 tos=0.13 msec
The full scale flow at 600,000 CFM.

FIG. 5 was used to produce a strip chart recording of the flow. The strip chart recorded $V_{10}$ as to 0 to 10 V signal.

$K_3$ and $K_4$ were determined so that a flow of 0 to 600,000 CFM would result in a 0 to 10 V signal out ($V_{10}$) as follows:
Let:

$$\frac{K_2}{K_3} t_d = 8\text{ V (somewhat arbitrary; } K_3 \text{ is used to keep } K_2 t_d \text{ out of voltage saturation)}$$

$$= V_5$$

Then
 $K_3 = K_{2/8}$ td
and
 $K_3$=3.662
 $V_{11}$=2$K_2$/$K_3$ tos, so
 $V_{11}$=0.1733
 $V_4 = V_5 - V_{11}$, or
 $V_4$=7.827
let:
 $V_2$=500 volts From Equation #23:

$$F = \frac{30ALK_2}{K_1}\left[\frac{V_2 - V_1}{(V_2 + K_2(t_d - 2t_{OS}))(V_1 + K_2(t_d - 2t_{OS}))}\right]$$

Solving for $V_1$ with the flow (F) at Full scale:

$$V_1 = 3.874$$

$$V_{10} = 100 K_4 \frac{V_2 - V_1}{\frac{V_2}{K_3} + V_4 \frac{V_1}{K_3} + V_4}$$

Solving for $K_4$:
 $K_4$=7.253
The resulting equation for $V_{10}$ where:
 $V_{10}$=10 volts represents 600 KCFM:

$$V_{10} = 725.3\left[\frac{V_2 - V_1}{\left(\frac{V_2}{3.662} + 7.827\right)\left(\frac{V_1}{3.662} + 7.827\right)}\right]$$

Thus, the flow is 600 KCFM when $V_1$=3.874 and $V_2$=5.000.

Although I have described and illustrated a present preferred apparatus and methods of using same, it should be distinctly understood that the invention is not limited thereto but may be variously embodied within the scope of the following claims.

I claim:

1. A method of ultrasonic measurement of a time taken by an ultrasonic tone burst to traverse a medium comprising the steps of:
 (a) placing a first transducer, said first transducer being capable of emitting a first ultrasonic signal upon receipt of a first electric signal and generating a first output electrical signal upon receipt of a second ultrasonic signal;

(b) placing a second transducer at a distance from the first transducer, said second transducer being capable of emitting the second ultrasonic signal upon receipt of a second electrical signal and generating a second output electrical signal upon receipt of the first ultrasonic signal;

(c) emitting the first ultrasonic signal from the first transducer to the second transducer thereby producing a second output signal;

(d) checking the second transducer for the second output signal during sequential time slots along a chosen time interval;

(e) producing a sequence of input samples, one for each time slot, according the presence and strength of the output signal at each time slot;

(f) selecting an address in a memory which corresponds to each time slot;

(g) storing each input sample in memory at an address which corresponds to the time slot at which the input sample was taken;

(h) emitting from the first transducer additional ultrasonic signals;

(i) checking after emission at each additional ultrasonic signal the second transducer for an output signal at the sequential time slots along the previously chosen time interval;

(j) producing a subsequent sequence of input samples, one for each time slot according to the presence and strength of the output signal at each time slot;

(k) mathematically combining each subsequent sequence of input samples to the input samples stored in memory thereby producing a corresponding new processed sample at each address;

(l) examining each new processed sample as to its degree of enhancement with a threshold value; and (m) measuring a traverse time by determining the time which corresponds time slot of the new processed sample which first reaches sufficient enhancement.

2. The method of claim 1 wherein the time slots are at intervals of 4 microseconds.

3. The method of claim 2 wherein one thousand twenty-four time slots are used thereby defining the time interval as 4.096 milliseconds.

4. The method of claim 1 also comprising the step of waiting an adjustable amount of time before checking for the output signal.

5. The method of claim 1 also comprising the additional steps following step m of:

(a) emitting a second ultrasonic signal from the second transducer to the first transducer thereby producing a first output signal;

(b) checking the first transduc.er for the first output signal during sequential time slots along a chosen time interval;

(c) producing a sequence of input samples, one for each time slot, according the presence and strength of the output signal at each time slot;

(d) selecting an address in a memory which corresponds to each time slot;

(e) storing each input sample in memory at an address which corresponds to the time slot at which the input sample was taken;

(f) emitting from the second transducer additional ultrasonic signals;

(g) checking the first transducer after emission of each additional ultrasonic signal for an output signal at the sequential time slots along the previously chosen time interval;

(h) producing a subsequent sequence of input samples, one for each time slot according to the presence and strength of the output signal at each time slot;

(i) mathematically combine each subsequent sequence of input samples with the input samples stored in memory thereby producing a corresponding new processed sample at each address;

(j) examining each new processed sample as to its degree of enhancement; and (k) measure the traverse time by determining the time which corresponds time slot of the new processed sample which first reaches sufficient enhancement.

6. The method of claim 1 also comprising the additional steps of:

(a) repeating steps c thru m after step m, (b) processing the times assigned to each time slot for which the processed sample has first reached a sufficiently enhanced value in each sequence of steps c thru m, and (c) calculating from such time a flow rate of the medium.

7. The method of claim 6 wherein the time slots are at intervals of 4 microseconds.

8. The method of claim 1 also comprising the additional step of calculating flow rate of the medium from the identified time.

9. The method of claim 1 also comprising the additional step of calculating the speed of the signal through the medium.

10. The method of claim 1 also comprising the steps of measuring the temperature of the medium and calculating the distance traveled by the signals through the medium from the measured temperature and identified time.

11. The method of claim 1 also comprising the steps (a) determining the ratio of the specific heat of the medium as a function of carbon dioxide concentration;

(b) calculating the specific heat of the medium using the identified time; and (c) calculating carbon dioxide concentration of the medium.

12. The method of claim 1 also comprising the step of calculating the temperature of the medium from the identified time.

13. An apparatus for measuring a time required for an ultrasonic signal to traverse a medium comprising:

(a) a pair of transducers positioned so that the medium is located between transducers both of which may alternately act as a transmitter and a receiver;

(b) a transducer driver connected to the transducers which when activated will cause the transducers to alternately transmit an ultrasonic signal;

(c) a timing control connected to the transmitter driver for activating the transmitter driver at selected times;

(d) an analog to digital convertor connected to the transducers and adapted to convert an analog signal received from a transducer into a digitized output comprised of a sequence of several words per signal each word corresponding to a predetermined time;

(e) a summation circuit adapted to serially combine each sequence of words received from the analog to digital convertor and output a signal whenever it receives a signal from the analog to digital convertor, said output being a combination of all sequences of words previously received from the analog to digital convertor; and (f) a monitoring circuit connected to the summation circuit adapted to compare each word of the summation circuit output to a predetermined level, and at least one voltage output identifies a time which corresponds to that word of the summation circuit output which first reaches the predetermined level the medium said time being the time required for the ultrasonic signal to traverse.

14. The apparatus of claim 13 wherein the summation circuit is a loop comprised of an adder, tristate buffer, memory and latch.

15. The apparatus of claim 13 wherein the monitoring circuit is comprised of:

(a) first and second level trips connected to the summation circuit;

(b) first and second digital to analog convertors connected respectively to the first and second level trips;

(c) an AND gate connected to the first and second level trips; and (d) first and second sample and hold components connected to the AND gate and respectively to the first and second digital to analog convertor.

16. The apparatus of claim 13 also comprising an analog circuit connected to the monitoring circuit adapted to convert a voltage received from the monitoring circuit to a flow rate of the medium.

17. The apparatus of claim 13 also comprising an analog circuit connected to the monitoring circuit adapted to convert a voltage received from the monitoring circuit to a speed at which sound passes through the medium.

18. The apparatus of claim 17 also comprising:

(a) a memory containing an algorithm that states speed of sound through the medium as a function of temperature; and (b) a processing unit connected to the memory and the analog circuit and adapted to convert the speed of sound received from the analog circuit to a temperature of the medium using the algorithm in the memory.

19. The apparatus of claim 13 also comprising:

(a) a temperature probe inserted in the medium and adapted to produce a voltage that corresponds to the medium's temperature; and (b) an analog circuit connected to the monitoring circuit and the temperature probe adapted to convert voltages received from the monitoring circuit and the temperature probe to a ratio of the specific heats of the medium.

20. The apparatus of claim 19 also comprising:

(a) a memory containing carbon dioxde concentrations and corresponding various ratios of specific heats of the medium;

(b) a processing unit connected to the memory and the analog circuit, adapted to compare the ratios specific heat identified by the analog circuit to the ratio of specific heats stored in the memory, match the identified ratio with an equivalent ratio of specific heats in the memory and report the carbon dioxide concentration which corresponds to that equivalent ratio specific heats.

21. The apparatus of claim 13 also comprising:

(a) a time multiplexer connected to the transducers for receiving a signal from each transducer when it is in the receiving mode and connected to the analog to digital converter.

22. The apparatus of claim 20 also comprising an automatic gain control connected between the time multiplexer and the analog to digital converter.

* * * * *